(12) United States Patent
Foody et al.

(10) Patent No.: US 8,247,200 B2
(45) Date of Patent: *Aug. 21, 2012

(54) METHOD OF OBTAINING INORGANIC SALT AND ACETATE SALT FROM CELLULOSIC BIOMASS

(75) Inventors: Brian Foody, Ontario (CA); Jeffrey S. Tolan, Ontario (CA)

(73) Assignee: Iogen Energy Corporation, Ontario (CA)

( * ) Notice: Subject to any disclaimer, the term of this patent is extended or adjusted under 35 U.S.C. 154(b) by 1217 days.

This patent is subject to a terminal disclaimer.

(21) Appl. No.: 12/018,989

(22) Filed: Jan. 24, 2008

(65) Prior Publication Data

US 2008/0182305 A1 Jul. 31, 2008

Related U.S. Application Data

(60) Provisional application No. 60/886,550, filed on Jan. 25, 2007.

(51) Int. Cl.
*C12P 7/54* (2006.01)
(52) U.S. Cl. ..................................................... 435/140
(58) Field of Classification Search .................. 435/140
See application file for complete search history.

(56) References Cited

U.S. PATENT DOCUMENTS

| | | | |
|---|---|---|---|
| 4,101,338 A | 7/1978 | Rapaport et al. | |
| 4,237,226 A | 12/1980 | Grethlein | |
| 4,356,196 A | 10/1982 | Hultquist | |
| 4,359,430 A | 11/1982 | Heikkila et al. | |
| 4,461,648 A | 7/1984 | Foody | |
| 4,600,590 A | 7/1986 | Dale | |
| 4,631,129 A | 12/1986 | Heikkila | |
| 5,037,663 A | 8/1991 | Dale | |
| 5,171,592 A | 12/1992 | Holtzapple et al. | |
| 5,407,580 A | 4/1995 | Hester et al. | |
| 5,536,325 A | 7/1996 | Brink | |
| 5,560,827 A | 10/1996 | Hester et al. | |
| 5,580,389 A | 12/1996 | Farone et al. | |
| 5,628,907 A | 5/1997 | Hester et al. | |
| 5,789,210 A | 8/1998 | Ho et al. | |
| 5,820,687 A | 10/1998 | Farone et al. | |
| 5,939,544 A | 8/1999 | Karstens et al. | |
| 5,968,362 A | 10/1999 | Russo, Jr. | |
| 6,106,888 A | 8/2000 | Dale et al. | |
| 6,176,176 B1 | 1/2001 | Dale et al. | |
| 6,482,268 B2 | 11/2002 | Hyoky et al. | |
| 6,663,780 B2 | 12/2003 | Heikkila et al. | |
| 6,709,527 B1 | 3/2004 | Fechter et al. | |
| 8,003,352 B2 * | 8/2011 | Foody et al. ........... | 435/72 |

FOREIGN PATENT DOCUMENTS

| | | |
|---|---|---|
| GB | 1 483 327 | 8/1977 |
| WO | 95/17517 | 6/1995 |
| WO | 02/070753 | 9/2002 |

OTHER PUBLICATIONS

Promega. Buffers for Biochemical Reactions, pp. 1-10, http://www.promega.com/resources/product-guides-and-selectors/protocols— Printed Sep. 23, 2011.*
Holtzapple et al. 1994. Saccharification, Fermentation, and Protein Recovery from Low-Temperature AFEX-Treated Coastal Bermudagrass. Biotechnology and Bioengineering, vol. 44, pp. 1122-1131.*
Grethlein, "Chemical Breakdown of Cellulosic Materials", J. Appl. Chem. Biotechnol., vol. 28 (1978) 296-308.
Nilvebrant et al., "Detoxification of Lignocellulose Hydrolysates with Ion-Exchange Resins", App. Biochem. Biotech., vol. 91-93 (2001) 35-49.
Wooley et al., "A Nine-Zone Simulating Moving Bed for the Recovery of Glucose and . . . ", Ind. Eng. Chem. Res., vol. 37 (1998) 3699-3709.
Nanguneri et al., "Acid/Sugar Separation Using Ion Exclusion Resins: A Process Analysis and Design", Sep. Sci. Tech., vol. 25, Nos. 13-15 (1990) 1829-42.
Bipp et al., "Application of ion exclusion chromatography (IEC) for the determination of sugar and . . . ", Fresenius J. Anal. Chem., vol. 357 (1997); 321-25.
Brennan et al., "High Temperature Acid Hydrolysis of Biomass Using an Engineering-Scale Plug . . . ", Biotech,. Bioeng. Symp. No. 17 (1986) 53-70.
Ghose, "Measurement of Cellulase Activities", Pure and Appl. Chem., vol. 59, No. 2 (1987) 257-68.
Miller, "Use of Dinitrosalicylic Acid Reagent for Determination of Reducing Sugar", Anal. Chem., vol. 31, No. 3 (1959) 426-28.

* cited by examiner

*Primary Examiner* — Jon P Weber
*Assistant Examiner* — Kailash C Srivastava
(74) *Attorney, Agent, or Firm* — Fitzpatrick, Cella, Harper & Scinto

(57) ABSTRACT

A process for obtaining inorganic salt and acetate salt from cellulosic biomass is disclosed. The cellulosic biomass is pretreated by adding one or more than one acid or base to produce a pretreated cellulosic biomass comprising acetic acid or acetate salt. One or more than one base or acid is then added to the pretreated cellulosic biomass to adjust the pretreated cellulosic biomass to a pH of about 4.0 to about 6.0 to produce a neutralized cellulosic biomass comprising inorganic salt and acetate salt. The neutralized biomass is then hydrolyzed by cellulase enzymes to produce a sugar stream. Streams arising from the processing of the cellulosic biomass to sugar are subjected to ion exclusion chromatography performed at pH 5.0 to about 10.0 to produce a stream comprising an inorganic salt and an acetate salt.

30 Claims, 6 Drawing Sheets

METHOD OF OBTAINING INORGANIC SALT AND ACETATE SALT FROM CELLULOSIC BIOMASS

This application claims benefit of U.S. Provisional Application No. 60/886,550 filed Jan. 25, 2007, the contents of which are herein incorporated by reference.

The present invention relates to a method of obtaining inorganic salt and acetate salt from cellulosic biomass, more particularly to a method of obtaining inorganic salt and acetate salt produced from the enzymatic conversion of cellulosic biomass to sugar.

BACKGROUND OF THE INVENTION

Fuel ethanol is currently produced from feedstocks such as cornstarch, sugar cane, and sugar beets. However, the production of ethanol from these sources cannot expand much further due to limited farmland suitable for the production of such crops and competing interests with the human and animal food chain. Finally, the use of fossil fuels, with the associated release of carbon dioxide and other products in the conversion process, is a negative environmental impact of the use of these feedstocks The possibility of producing fuel ethanol from cellulose-containing feedstocks, such as agricultural wastes, grasses, forestry wastes, and sugar processing residues has received much attention due to the availability of large amounts of these inexpensive feedstocks, the desirability to avoid burning or landfilling cellulosic waste materials, and the cleanliness of ethanol as a fuel compared to gasoline. In addition, a byproduct of the cellulose conversion process, lignin, can be used as a fuel to power the cellulose conversion process, thereby avoiding the use of fossil fuels. Studies have shown that, taking the entire cycle into account, the use of ethanol produced from cellulose generates close to nil greenhouse gases.

The cellulosic feedstocks that may be used for ethanol production include (1) agricultural wastes such as corn stover, wheat straw, barley straw, canola straw, and soybean stover; (2) grasses such as switch grass, miscanthus, cord grass, and reed canary grass; (3) forestry wastes such as aspen wood and sawdust; and (4) sugar processing residues such as bagasse and beet pulp.

Cellulose consists of a crystalline structure that is very resistant to breakdown, as is hemicellulose, the second most prevalent component. The conversion of cellulosic fibers to ethanol requires: (1) liberating cellulose and hemicellulose from lignin or increasing the accessibility of cellulose and hemicellulose within the cellulosic feedstock to cellulase enzymes; (2) depolymerizing hemicellulose and cellulose carbohydrate polymers to free sugars; and (3) fermenting the mixed hexose and pentose sugars to ethanol.

The feedstock is conveyed into the plant and the feedstock particles are typically reduced to the desired size to be suitable for handling in the subsequent processing steps. The next process step is a chemical treatment, which generally involves the use of steam or heated water along with acid or alkali to break down the fibrous material. The chemical treatment is carried out either as a direct conversion process—acid hydrolysis or alkali hydrolysis—or as a pretreatment prior to enzymatic hydrolysis.

In the acid or alkali hydrolysis process, the feedstock is subjected to steam and acid or alkali under conditions sufficient to hydrolyze the cellulose to glucose (Grethlein, *J. Appl. Chem. Biotechnol.*, 1978, 28:296-308). The glucose is then fermented to ethanol using yeast, and the ethanol is recovered and purified by distillation.

The enzymatic hydrolysis process involves pretreating the cellulosic material in a process that is analogous to the acid or alkali hydrolysis process described above, but using milder conditions. This pretreatment process increases the accessibility of cellulose within the cellulosic fibers for subsequent conversion steps, but results in little conversion itself. In the next step, the pretreated feedstock is adjusted to an appropriate temperature and pH for enzymatic conversion of cellulose by cellulase enzymes. The reaction conditions for the pretreatment process are chosen to be significantly milder than that in the acid or alkali hydrolysis process, such that the exposed cellulose surface area is greatly increased as the fibrous feedstock is converted to a muddy texture.

In the case of acid pretreatment, much of the hemicellulose is hydrolyzed, but there is little conversion of the cellulose to glucose. The cellulose is hydrolyzed to glucose in a subsequent step that uses cellulase enzymes, and the hydrolysis in this case is known as pretreatment. Alkali pretreatment methods may or may not hydrolyze hemicellulose. In either case, the base reacts with acidic groups present on the hemicellulose to open up the surface of the substrate. In addition, it has been reported that concentrated alkali alters the crystal structure of the cellulose so that it is more amenable to hydrolysis. The cellulose is then typically hydrolyzed to glucose in a subsequent step that uses cellulase enzymes, although it is possible to hydrolyze the cellulose, in addition to the hemicellulose, using acid hydrolysis after alkaline pretreatment.

The hydrolysis of the cellulose, whether by acid, alkali or by pretreatment followed by enzyme hydrolysis, may be followed by the fermentation of the sugar to ethanol, which is then recovered by distillation. Other fermentation products that may be produced include butanol and lactic acid.

The efficient conversion of cellulose from cellulosic material into sugars and the subsequent fermentation of sugars to ethanol or other valuable products represent a major challenge to the industry. In particular, a large amount of impurities, including salt, sugar degradation products, organic acids, soluble phenolic compounds, and other compounds are present in the sugar stream after the pretreatment. These compounds result from degradation of the feedstock or, in the case of the salts, from the acids and alkali added in the process. The presence of these impurities is highly inhibitory to the fermentation of the sugar by the yeast. In the absence of an efficient fermentation of the sugar in high yield, the production of ethanol from biomass is not commercially viable. Furthermore, the inability to recover acetic acid and salt from the sugar streams, due to the large amount of impurities present, represents a loss of potential revenue in the process.

The removal of toxic inhibitors, sulfuric acid and sulfate salts, and acetic acid and acetate salts from the sugar streams prior to fermentation has been the subject of a significant amount of research. The processes studied include lime addition, ion exchange, and ion exclusion.

In lime addition, lime (calcium hydroxide), which is insoluble, is added to the sugar stream to precipitate impurities. The limed sugar solution has an alkaline pH and is neutralized with acid, typically phosphoric acid, sulfurous acid, carbonic acid, or a mixture thereof. Optionally, the lime cake is separated from the sugar by filtration. A second option is to filter the lime cake at alkaline pH and carry out a second filtration to remove material that precipitates during the acidification steps. Lime treatment decreases the toxicity of the sugar stream to yeast and other microbes. However, any handling of the lime cake is difficult and costly. In addition, the introduction of calcium into the stream increases the likelihood that calcium scale will deposit on evaporators, distillation columns, and other process equipment. The clean-up and avoidance of scale increases the cost of sugar processing. Furthermore, the introduction of lime makes the recovery of salt and acetic acid more difficult.

In ion exchange, the sugar stream is flowed through columns packed with ion exchange resins. The resins are in a cation exchange or anion exchange form, or a combination of the two. In principle, cation-exchange resins remove cations such as sodium or potassium, while anion-exchange resins remove anions such as sulfate and acetate. For example, ion exchange has been investigated by Nilvebrant et al. (*App. Biochem. Biotech.*, 2001, 91-93:35-49) in which a spruce hydrolyzate was treated to remove fermentation inhibitors, such as phenolic compounds, furan aldehydes and aliphatic acids. The separation was carried out using an anion exchanger, a cation exchanger and a resin without charged groups. The investigators found that treatment at pH 10.0 using an anionic exchanger removed phenolic inhibitors since at this pH most of the phenolic groups were ionized.

In practice, several factors limit the effectiveness of ion exchange treatment to remove inhibitors. First, the multicomponent nature of the streams results in an inefficient removal of some species at any single set of conditions. Second, the high ionic load demands very frequent and expensive regeneration of the resin. Finally, not all of the inhibitors are ionic, and ion exchange is ineffective in removing nonionic compounds from sugar.

Ion exclusion uses ion exchange resins, but rather than bind target ions in solution, the charge on the resin matches that of the target ions in the solution, thereby excluding them from the resin. The excluded compounds then elute from the column readily, while uncharged compounds absorb into the resin and elute from the column more slowly. For example, a concentrated solution of sulfuric acid and glucose has hydrogen as the primary cation. A cation-exchange resin in the hydrogen form will exclude the acid, causing it to elute quickly. The glucose, which is uncharged, is not excluded from the resin and absorbs into the resin void, thereby eluting from the column more slowly than the acid.

Ion exclusion for detoxification of sugars from biomass streams has been described by various groups. For example, Wooley et al., (*Ind. Eng. Chem. Res.*, 1998, 37:3699-3709) teaches the removal of acetic acid and sulfuric acid from biomass sugars by pumping a product stream over a bed of cation exchange resin in the hydrogen form. The positive charge on the resin repels the hydrogen ion in the sulfuric acid, thereby causing the sulfuric acid to elute from the column very quickly. The uncharged sugar molecules are absorbed into the void space of the resin and elute from the column more slowly than the sulfuric acid. Fully associated acetic acid (non-ionic) is a smaller molecule than sugar or sulfuric acid and so elutes from the column more slowly than sulfuric acid or sugar. Also described is a Simulated Moving Bed (SMB) system for producing a glucose stream free of sulfuric acid and acetic acid. A shortcoming of Wooley's process is that the glucose recovery is only 92%. The 8% loss of glucose represents a significant cost in the system. The ion exclusion was carried out at a pH of between about 1-2 and, at such low pH values, significant degradation of xylose is likely.

U.S. Pat. Nos. 5,560,827 and 5,628,907 (Hester et al.) disclose a process for separating an ionic component (acid) from a non-ionic component (sugar) using an SMB arrangement, including a plurality of ion exclusion columns arranged in 4 zones. The separations are run at a low pH using a cationic (or cation-exchange) resin in the hydrogen form. The methods of Hester incorporate various arrangements to minimize the dispersion and channeling effects. The sugar/acid solution is loaded onto the column and the acid elutes first while sugar is eluted later using water.

U.S. Pat. No. 5,407,580 (Hester et al.) discloses a process for separating an ionic component (acid) from a non-ionic component (sugar) using a preparative-scale ion exclusion system. The system includes a floating head distribution plate to prevent evolution of a dilution layer caused by the shrinkage of the resin bed. The columns can be operated over a range of process conditions to produce separate and distinct elution profiles for the acid and sugar. Acceptable conditions for carrying out the process are at a sulfuric acid concentration of 1.0 to 20.0 wt % (fed to the top of the column), a feed volume of 1.0 to 5.0 (percent of empty column volume), a flux rate of 0.1 to 2.0 (cm/min) and using a divinylbenzene resin with a percent crosslinking of between 1.0 and 15% (percent divinylbenzene cross-linking).

U.S. Pat. Nos. 5,580,389 and 5,820,687 (Farone et al.) teach a method of producing and separating sugars. The two-step method involves decrystallizing and hydrolyzing biomass using acid, then pressing the hydrolyzate and collecting the liquid, which contains acid and sugars. The liquid is loaded onto a cross-linked strong cation exchange resin run at low pH, where the sugars adsorb to the resin. The resin is purged with gas, pushing the acid out of the resin; the resin is then washed with water, producing a sugar stream.

U.S. Pat. No. 5,968,362 (Russo et al.) discloses a method of separating sugars and acid by ion exclusion chromatography using an anion exchange resin. The sugars elute through the column, and may contain residual acid and heavy metals. The heavy metals can be removed and the acid neutralized using a lime treatment. The acid adsorbs to the resin and is retained; it is eluted from the resin with water.

Nanguneri et al. (*Sep. Sci. Tech.*, 1990, 25(13-15):1829-1842) simulated the separation of sugars from acids using a modified mathematical model and compared the results obtained with experimental data. Separation performances at different process parameters were then analyzed to determine optimal processing conditions. The simulated process would result in an acid-rich stream eluting first, followed by a dilute acid/sugar interface stream and then a sugar-rich stream. Nanguneri et al. performed an economic analysis at the optimal processing conditions and concluded that ion exclusion is highly feasible for the processing of lignocellulosic feedstocks to produce ethanol. However, a drawback of the method of Nanguneri et al. is that the dilute acid/sugar interface stream is costly to separate and recover.

U.S. Pat. No. 6,663,780 (Heikkilä et al.) discloses a method in which product fractions, such as sucrose, betaine and xylose, are separated from molasses that are obtained from a variety of sources, including beet and cane molasses, as well as hydrolyzates produced from biomass. The process involves treating the molasses with sodium carbonate (pH 9) to precipitate calcium followed by removing the resulting precipitate. The filtrate is then subjected to a simulated moving bed (SMB) process which is carried out using at least two SMB systems packed with a strongly acid cation exchange resin. Sucrose is recovered in a first system and betaine is recovered in a second system. The sucrose obtained from the first system may be crystallized and the crystallization run-off applied to the second system. Also described is a process for recovering xylose from sulphite cooking liquor using two systems. Prior to fractionation in the first system, the sulphite cooking liquor, having a pH of 3.5, is filtered and diluted to a concentration of 47% (w/w). The xylose fractions obtained from the first system are crystallized and, after adjustment to pH 3.6 with MgO, the run-off is fed to the second system. In the second system, a sequential SMB is used to separate xylose from the crystallization run-off.

A disadvantage of the separation technique disclosed in U.S. Pat. No. 6,663,780 (Heikkilä et al.) is that the inclusion of two SMB systems is costly and adds to the complexity of the process. In addition, sugars present in a hydrolyzate produced by the processing of lignocellulosic biomass are much more difficult to crystallize than sucrose in a beet process. The initial sucrose purification by crystallization in U.S. Pat. No. 6,663,780 is not successful with glucose in biomass systems.

Various groups have reported the separation of sucrose from molasses obtained from sugar cane using ion exclusion chromatography or ion exchange. For example, U.S. Pat. No. 4,359,430 (Heikkilä et al.) discloses a method of recovering betaine from inverted molasses. The molasses are first diluted with water to a concentration of 35-40% and then applied to a column containing a cation exchange resin. On elution with water, a first non-sugar waste fraction is obtained, followed by a second sugar-containing fraction, and a third fraction containing betaine. The betaine is recovered by evaporation and crystallization. Although high levels of betaine are recovered, the patent does not address the recovery of sucrose from the sugar-containing fraction.

U.S. Pat. No. 6,482,268 (Hyöky et al.) also discloses a method of separating sucrose and betaine from beet molasses by a simulated moving bed (SMB) process. Similar to U.S. Pat. No. 6,663,780, the method of Hyöky et al. involves first precipitating calcium from the beet molasses by adding sodium carbonate and filtering the resulting calcium carbonate by filtration. The beet molasses are next applied to a column packed with a strong cation exchanger resin with a divinylbenzene backbone. A sucrose fraction is eluted first, followed by a betaine fraction, which is then concentrated and further fractionated to yield a second sucrose fraction and a second betaine fraction containing some sucrose. The second sucrose and betaine fractions are combined with the sucrose and betaine fractions obtained from the initial fractionation. Although Hyöky et al. describe the separation of sucrose and betaine from beet molasses, in a biomass conversion process, these components would not be present.

A method of separating sugar from molasses using ion exclusion chromatography is taught in GB 1,483,327 (Munir et al.). The ion exclusion column comprises two types of cation exchange resins used in the salt form to help prevent shrinkage of the column bed. Sugar adsorbs to the column and is eluted using decarbonized water adjusted to a pH of greater than 9.

WO 95/17517 (Chieffalo et al.) discloses a method of processing municipal solid waste to recover reusable materials and to make ethanol. Cellulosic material is shredded and pre-treated with acid and lime to remove heavy metals, then treated with concentrated acid (sulfuric) to produce sugars. The sugars and the acid are separated on a strong acidic cation ion exchange resin.

U.S. Pat. No. 4,101,338 (Rapaport et al.) discloses a method of separating salts and sucrose present in blackstrap molasses obtained from sugar cane by ion exclusion chromatography. Prior to ion exclusion chromatography, the molasses are treated by removing organic non-sugar impurities and colour. Various methods are suggested for removing these impurities, including a preferred method utilizing precipitation with iron salts, such as ferric chloride or ferric sulfate, to form flocs. The insoluble flocs are then removed from the molasses stream and the soluble iron salts are removed by the addition of lime and phosphoric acid or inorganic phosphate salts, which raises the pH to above 7.0. The molasses stream is then applied to the ion exchange column to produce fractions containing sucrose and separated salts. A disadvantage of this process is that, upon addition of ferric ions, the molasses has a pH that is in the range of 2.0 to 3.0. At such a low pH, degradation of xylose could occur. Furthermore, Rapaport et al. do not address the separation of acetic acid from sugars.

Organic non-carbohydrate impurities within a lignocellulosic system cannot be removed by the methods of Rapaport et al. According to the method of Rapaport, the amount of solids precipitated by iron salts or ethanol is modest and no solids are removed by centrifugation. By contrast, the sugar streams produced during the processing of lignocellulosic feedstock have a much higher level of organic non-carbohydrate impurities and inorganic salts. Rapaport et al. do not address the processing of such concentrated streams.

U.S. Pat. No. 6,709,527 (Fechter et al.) discloses a process of treating an impure cane-derived sugar juice to produce white sugar and white strap molasses. The process involves subjecting the sugar juice to microfiltration/ultrafiltration to decrease the levels of impurities. The sugar juice is next subjected to ion exchange with a strong acid cation exchange resin in the hydrogen form and then to ion exchange with an anion exchange resin in the hydroxide form. After ion exchange, the resulting sugar solution is concentrated to produce syrup which is then crystallized to produce impure crystallized sugar and white strap molasses. Although the process results in the removal of impurities from the sucrose solution, it would be subject to the limitations associated with ion exchange chromatography described above.

U.S. Pat. No. 4,631,129 (Heikkilä et al.) teaches a method of purifying sugar from a sulfite pulping spent liquor stream. The process involves two steps, in which, during the first step, the pH of the spent sulfite liquor is adjusted to below 3.5 and the stream is passed through a strongly acidic ion exclusion resin to recover two lignosulfonate-rich raffinate fractions and a product stream containing the sugar and consisting of 7.8%-55% lignosulfonate. In the second step, the product stream is adjusted to pH 5.5-6.5. The product stream is then filtered, and applied to a second ion exclusion column to further purify the sugar by separating it from the large amount of lignosulfonates in this stream. A problem with this process is that the use of two ion exclusion systems is costly and adds to the complexity of the process. Moreover, Heikkilä et al. do not quantify or address the separation of compounds present during the processing of biomass such as inorganic salts, including sulfate salts, and acetic acid and other organic acids.

Bipp et al. (*Fresenius J. Anal. Chem.*, 1997, 357:321-325) describes the analytical determination and quantification of sugar acids and organic acids from whey powder hydrolyzates by ion exclusion chromatography. The elution was carried out with 0.005 M sulfuric acid (pH of 2.3) at a temperature of 45° C. and 0.05 M (pH of 1.30) and a temperature of 10° C. Although the analysis demonstrated that the method was suitable for the determination and quantification of organic acids, including sugar acids and acetic acid, the temperatures required for the separation would not be practical in an industrial application. Furthermore, such low pH values would likely result in the production of degradation products.

There is a need for an economical system for obtaining inorganic salt and acetate salt from processing of a cellulosic biomass. The development of such a system remains a critical requirement for the overall process to convert lignocellulosic feedstocks to glucose and subsequently to ethanol or other products.

SUMMARY OF THE INVENTION

The present invention relates to a method of producing a salt stream comprising inorganic salt and acetate salt from cellulosic biomass, more particularly to a method of obtaining inorganic salt and acetate salt produced from the enzymatic conversion of cellulosic biomass to sugar.

It is an object of the present invention to provide a method of biomass conversion having improved performance.

The process of the present invention overcomes the disadvantages of the prior art by operating an ion exclusion at a much higher pH range than that previously reported for process streams arising from biomass conversion processes. The present invention is based on the discovery that at pH values of about 5-10, inorganic salts produced during processing of the cellulosic biomass and acetate salts arising from the pretreatment are excluded by a cation exclusion resin. This results in a similar elution of the inorganic and acetate salts at pH 5 to 10, thereby eliminating the need for using two streams to obtain inorganic salt and acetic acid that is required at more acidic conditions. This, in turn, decreases the complexity of the system.

Therefore, the invention offers significant advances in obtaining inorganic and acetate salts during the conversion of lignocellulosic feedstocks. The stream fed to the ion exclusion separation may arise from a variety of different streams produced during the processing of the cellulosic biomass to produce sugar. In one embodiment, the invention provides for the removal of inorganic salt and acetate salt from a sugar stream produced by enzyme hydrolysis. This purified sugar stream may then be fermented to produce ethanol or butanol. In another embodiment of the invention, inorganic salt and acetate salt are removed from an aqueous stream obtained from a cellulosic biomass pretreated with acid or base.

This summary of the invention does not necessarily describe all necessary features of the invention.

BRIEF DESCRIPTION OF THE DRAWINGS

These and other features of the invention will become more apparent from the following description in which reference is made to the appended drawings wherein:

FIG. 2 shows separation of glucose and sodium sulphate and sodium acetate using ion exclusion chromatography at different pH values.

FIG. 5 shows the separation of xylose from salts in a biomass conversion process using ion exclusion chromatography performed at pH 5.

DESCRIPTION OF PREFERRED EMBODIMENTS

Figure 1:
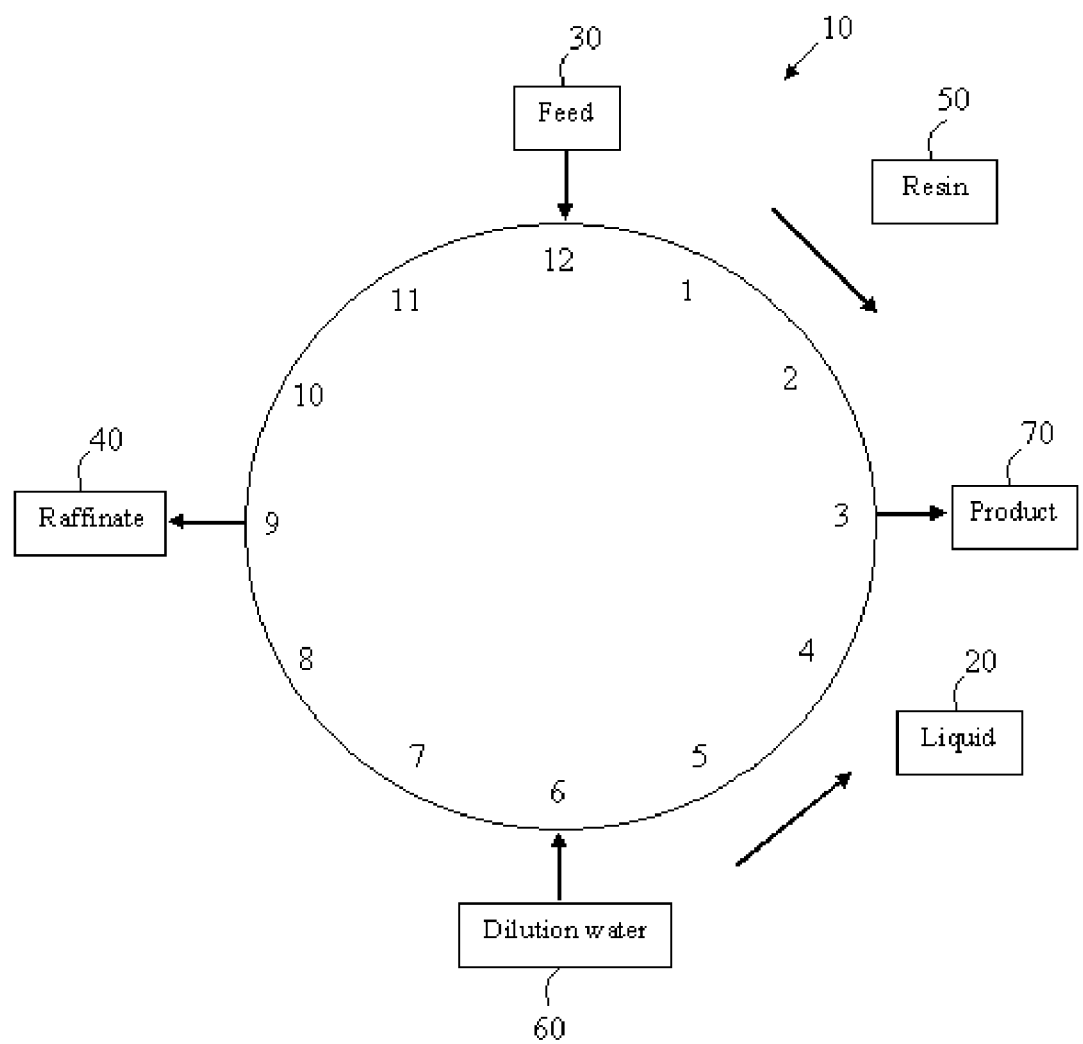
FIG. 1 shows a representation of the zones and liquid flows in a Simulated Moving Bed (SMB) system.

The present invention relates to a method of obtaining inorganic salt and acetate salt from cellulosic biomass, more particularly to a method of obtaining inorganic salt and acetate salt produced from the enzymatic conversion of cellulosic biomass to sugar.

The following description is of a preferred embodiment.

The process of the present invention allows for the removal of acetate salt and inorganic salts from streams that originate during the conversion of a lignocellulosic feedstock to sugar.

The sugar stream is the product of the conversion of a cellulosic feedstock to sugar by hydrolysis. By the term "lignocellulosic feedstock", "lignocellulosic biomass", "cellulosic biomass", or "biomass feedstock", it is meant any type of biomass comprising cellulose. Cellulosic biomass can consist of an entire plant or a portion thereof, or a mixture of plants or portions thereof, whichever may be the source of crude sugar for the process. The process of the invention is effective on a wide variety of biomass feedstocks, including: (1) agricultural wastes such as corn stover, corn fiber, wheat straw, barley straw, canola straw, oat straw, rice straw, and soybean stover; (2) grasses such as switch grass, miscanthus, cord grass, and reed canary grass; (3) forestry residues such as aspen wood and sawdust; (4) sugar residues, such as bagasse or beet pulp; and any combination thereof.

Cellulosic biomass comprises cellulose in an amount greater than about 20%, more preferably greater than about 30%, more preferably greater than about 40% (w/w), still more preferably greater than 50% (w/w). For example, the lignocellulosic material may comprise from about 20% to about 50% (w/w) cellulose, or more, or any amount therebetween. The cellulosic biomass may also contain lignin at an amount between greater than about 10%, or, more typically, in an amount greater than about 15% (w/w).

It is preferred that the feedstocks do not comprise molasses or spent sulfite liquor. Greater than about 80%, preferably greater than about 85% or 90% of the sugar in the sugar stream is the result of hydrolysis of cellulose and hemicellulose in the cellulosic feedstock. For example, 80, 82, 85, 87, 90, 92, 95, 97, or 100% of the sugar in the sugar stream may be derived from cellulose and hemicellulose. Furthermore, it is preferred that at least 50, 55, 60, 65, 70, 75, 80, 85 or 90 wt % of the cellulose in the biomass is converted to glucose.

The sugars may be produced by any method known in the art, for example, but not limited to, subjecting the feedstock to acid or alkali hydrolysis (e.g. as disclosed in Brennan et al, Biotech, Bioeng. Symp. No. 17, 1986, which is incorporated herein by reference). The acid or alkali hydrolysis may be carried out to convert the cellulose to glucose, convert a portion of the cellulose to glucose, convert the hemicellulose to its monomeric sugars of xylose, arabinose, galactose, mannose, convert a portion of the hemicellulose to its monomeric sugars, or a combination thereof.

The acid used for acid hydrolysis may be any type of suitable acid known in the art, including, but not limited to, sulfuric acid. Sulfuric acid may be used in a dilute form from about 0.1% to about 5% on weight of feedstock or any amount therebetween, or the sulfuric acid may be used in a concentrated form, for example, submersing the feedstock in from about 30% to about 80%, or any amount therebetween, solution of acid, by weight. It is preferred that the crude sugar stream is characterized as having a lignosulfonate content of less than 10% of the total dry solids of the crude sugar stream. For example, crude sugar streams characterized as having an amount of lignosulfonate from about 0 to about 10% of the total dry solids of the crude sugar stream, or about 10, 8, 6, 4, 2, 1 or 0% of the total dry solids of the crude sugar stream, may be used in the process described herein.

The cellulosic biomass may be subjected to a pretreatment to increase the susceptibility of the cellulosic biomass to hydrolysis by cellulase enzymes. This may involve subjecting the biomass feedstock to an acidic pretreatment process to convert hemicellulose, a portion of the cellulose, a portion of the hemicellulose, or any combination thereof, to sugar, and the remaining cellulose may then be converted to glucose by enzymatic hydrolysis with cellulase enzymes. The acidic pretreatment is carried out to convert at least a portion of hemicellulose to xylose, arabinose, galactose, mannose and a small portion of the cellulose to glucose, and the remaining cellulose is then converted to glucose by enzymatic hydrolysis with cellulase enzymes. A non-limiting example of such a treatment includes steam explosion, as described in U.S. Pat. No. 4,461,648 (Foody; which is incorporated herein by reference). Generally, acidic pretreatment conditions for lignocellulosic feedstocks comprise a temperature in the range of about 170° C. to about 260° C., or any amount therebetween, for a period of about 0.1 to about 30 minutes or any amount therebetween, and at a pH of about 0.4 to about 2.0 or any amount therebetween.

Examples of other acid pretreatment processes that are suitable for the practice of this invention, which are not to be considered limiting, include those described in U.S. Pat. No. 5,536,325; U.S. Pat. No. 4,237,226; and Grethlein, *J. Appl. Chem. Biotechnol.*, 1978, 28:296-308; which are incorporated herein by reference. After pretreatment, the pH of the material is adjusted to the appropriate range prior to enzymatic hydrolysis.

The low pH for acid pretreatment may involve the addition of dilute acid, added to achieve a final concentration in the feedstock from about 0.02% (w/v) to about 3% (w/v), or any amount therebetween. The acid used for pretreatment may be any type of suitable acid known in the art, including, but not limited to, sulfuric acid, or phosphoric acid. Sulfuric acid is preferred due to its low cost and, following recovery, its use in fertilizer in the form of sulfate salts. The term "sulfate salts" includes bisulfate salts that are also present, at a concentration that depends on the pH.

Alternatively, the pretreatment involves the addition of base to produce an alkali pretreated feedstock. Without wishing to be bound by theory, alkali pretreatment sometimes does not hydrolyze hemicellulose, but rather the base reacts with acidic groups present on the hemicellulose to open up the surface of the substrate and produce acetate salt. In addition, the base may alter the crystal structure of the cellulose so that it is more amenable to hydrolysis.

Alkali that may be used in the pretreatment includes ammonia, ammonium hydroxide, potassium hydroxide, and sodium hydroxide. The base is preferably soluble in water, which excludes lime or magnesium hydroxide.

An example of a suitable alkali pretreatment is Ammonia Freeze Explosion, or Ammonia Fiber Explosion ("AFEX" process). According to this process, the cellulosic biomass is contacted with ammonia or ammonium hydroxide in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592 which are incorporated herein by reference.) The flashed ammonia may then be recovered according to known processes.

The step of pretreating the feedstock with ammonia or ammonium hydroxide may be performed at a temperature between about 20° C. to about 200° C., or any temperature therebetween. For example, the temperature may be 20, 40, 60, 80, 100, 120, 140, 160, 180, or 200° C. The pH is typically from about pH 9.5 to about pH 12, or any pH therebetween. For example, the pH of the feedstock may be 9.5, 9.8, 10.0, 10.2, 10.4, 10.6, 10.8, 11.0, 11.2, 11.4, 11.6, 11.8 or 12.0. The treatment time may be from 2 minutes to about 120 minutes, or any amount of time therebetween. For example, the duration of the pretreatment may be 2, 3, 4, 5, 6, 7, 8, 9, 10, 11, 12, 13, 14, 15, 16, 17, 18, 19, 20, 30, 40, 50, 60, 70, 80, 90, 100, 110 or 120 minutes. The moisture content of the feedstock may be between 50% and 70%, or any range therebetween; for example, the moisture content may be 50, 52, 54, 56, 58, 60, 62, 64, 66, 68 or 70%. The ammonia or ammonium hydroxide is added to achieve a concentration which is generally about 0.5 to about 2.5 times the mass of the feedstock on a dry basis, or any amount therebetween. For example, the ammonia concentration may be about 0.5, 0.7, 0.8, 0.9, 1.0, 1.2, 1.4, 1.6, 1.8, 2.0, 2.2, 2.4 or 2.5 times the mass of the feedstock on a dry basis.

If the feedstock is pretreated with sodium hydroxide or potassium hydroxide, the temperature may be between about 50° C. to about 220° C., or any temperature range therebetween. For example, the temperature may be 50, 60, 70, 80, 90, 100, 110, 120, 130, 140, 150, 160, 170, 180, 190, 200, 210 or 220° C. The pH is typically between about 10 to about 13, or any pH range therebetween. For example, the pH may be 10.0, 10.5, 11.0, 11.5, 12.0, 12.5 or 13.0. The treatment time may be from about 15 minutes to about 120 minutes, or any range therebetween. In a non-limiting example, the treatment time is 15, 20, 30, 40, 50, 60, 70, 80, 90, 100, 110 or 120 minutes.

The pretreated cellulosic biomass is enzymatically hydrolyzed with cellulase enzymes. Cellulase enzymes can typically tolerate a range of pH of about 4 to 6; therefore, the pretreated feedstock is generally neutralized prior to enzymatic hydrolysis. A pH more favorable to the cellulase enzymes is, for example, within the range of about 4.5 to about 5.0, or any value therebetween. If the feedstock is pretreated with base, the enzymatic hydrolysis may further comprise the addition of xylanase enzymes.

The term "base" is meant to encompass any soluble species that, when added to water, gives a solution with a pH that is more than 7, and which is suitable for neutralizing the feedstock after acid pretreatment to a pH value that is compatible with enzymes used during enzymatic hydrolysis.

In the case of acid pretreatment, the pH adjustment is preferably carried out using a soluble base. By the term "soluble base", it is meant a base that has a solubility in water that is at least 0.1 M at 20° C. This term is meant to exclude salts that are slightly soluble or insoluble. Examples of insoluble bases that are excluded from the definition of soluble base are $CaCO_3$ and $Ca(OH)_2$. Non-limiting examples of soluble bases include sodium hydroxide, potassium hydroxide, ammonia, and ammonium hydroxide.

When an alkali pretreatment is performed, the pH adjustment after pretreatment involves addition of an acid. Non-limiting examples of acids that may be used are sulfuric acid, sulfurous acid, sulfur dioxide, phosphoric acid, carbonic acid, carbon dioxide, hydrochloric acid, or a combination thereof. In the case of a pretreatment carried out with ammonia or ammonium hydroxide, the pH may be adjusted with sulfuric acid, phosphoric acid, hydrochloric acid, carbon dioxide/carbonic acid or sulfurous acid which produces the inorganic salts ammonium sulfate, ammonium phosphate, ammonium chloride, ammonium carbonate or ammonium sulfite, respectively. If potassium hydroxide is used in the pretreatment, the feedstock may be neutralized with phosphoric acid to produce potassium phosphate. These inorganic salts may be used directly as a fertilizer or, in the case of ammonium sulfate or ammonium carbonate, subjected to degradation reactions to produce ammonia, which, in turn, may be recovered and/or recycled in the process.

For example, ammonium carbonate may be decomposed to produce ammonia and carbon dioxide. The decomposition may involve thermal treatment to liberate the ammonia and carbon dioxide. The ammonia and/or the carbon dioxide may then be recovered, for example, by distillation, stripping or evaporation. The recovered ammonia may, in turn, be recycled to the alkaline pretreatment step.

Preferably, the alkali pretreatment comprises addition of ammonia or ammonium hydroxide, followed by neutralization with sulfuric acid to produce ammonium sulfate. It will be understood by those of skill in the art that the ammonia may be provided in anhydrous form. The ammonium sulfate produced during the neutralization may be used directly as a fertilizer, or, alternatively, may be subjected to thermal decomposition according to the method of co-pending U.S. application entitled "Process for Producing Ammonia and Sulfuric Acid from a Stream Comprising Ammonium Sulfate" (Curren et al.) to produce sulfuric acid and sulfate salts, such as ammonium sulfate.

The acid or alkali requirement for pretreatment may be decreased by removing salts from the feedstock prior to pretreatment. Salts may be removed by washing, leaching, or a combination of these processes. One form of the leaching process is taught in WO 02/070753 (Griffin et al., which is incorporated herein by reference). This process involves contacting the feedstock with water for two minutes or longer, then separating the solids from the aqueous phase ("leachate") by pressing or filtration. After leaching, the aqueous phase contains potassium and other salts and trace elements. This process may not only decrease costs, but may also decrease the degradation of xylose in the pretreatment process.

By the term "cellulase enzymes", "cellulase", or "enzymes", it is meant enzymes that catalyse the hydrolysis of cellulose to products such as glucose, cellobiose, and other cellooligosaccharides. Cellulase is a generic term denoting a multienzyme mixture, produced by a number of microorganisms, comprising exo-cellobiohydrolases (CBH), endoglucanases (EG) and β-glucosidases (βG). Among the most widely studied, characterized, and commercially produced cellulases are those obtained from fungi of the genera *Aspergillus, Humicola,* and *Trichoderma,* and from the bacteria of the genera *Bacillus* and *Thermobifida.* In a non-limiting example, the pretreated feedstock may be submitted to hydrolysis by cellulase enzymes produced by *Trichoderma.*

The cellulase enzyme dosage is chosen to convert the cellulose of the feedstock to glucose to produce a crude sugar stream. For example, an appropriate cellulase dosage can be about 5.0 to about 50.0 Filter Paper Units (FPU or IU) per gram of cellulose, or any amount therebetween. For example, the cellulase dosage may be about 5, 8, 10, 12, 15, 18, 20, 22, 25, 28, 30, 32, 35, 38, 40, 42, 45, 48, or 50 FPU, or any amount therebetween. The FPU is a standard measurement which is familiar to those skilled in the art and is defined and measured according to Ghose (*Pure and Appl. Chem.,* 1987, 59:257-268).

The crude sugar stream produced by the enzymatic hydrolysis is preferably clarified. Any suitable method for removing insoluble residue from the crude sugar stream to produce a clarified sugar stream can be employed as would be known by one of skill in the art. This includes, but is not limited to, microfiltration, plate and frame filtration, crossflow filtration, pressure filtration, vacuum filtration, centrifugation and the like.

The soluble compounds in the clarified sugar stream may include monomeric sugars such as glucose, xylose, arabinose, galactose, mannose, and oligomers of these sugars; acetic acid, sulfuric acid, lactic acid, oxalic acid, among other organic acids, and the salts of these acids; cations including sodium, calcium, potassium, ammonium, magnesium, and others; anions, in addition to the organic acids named above, including silicate, phosphate, and carbonate. Preferably, the solids in the clarified sugar stream are comprised of at least 30 wt % sugar; for example, the solids in the clarified sugar stream may comprise more than 30, 35, 40, 45, 50, 55, 60, 65, 70, 75, 80, 85, 90, or 95 wt % sugar. It is also preferred that the minimum concentration of acetic acid and acetate salts in the clarified sugar stream is about 5 g/L. A variety of other compounds are present in the clarified sugar stream, including sugar degradation products such as furfural and hydroxymethyl furfural, and soluble phenolic compounds derived from lignin. Organic extractive compounds, such as soaps and fatty acids, are also present.

As described in more detail below, a stream obtained during processing of the cellulosic biomass (referred to herein as a "feed stream") is treated by ion exclusion chromatography to separate sugars or other nonionic compounds from inorganic salts and other ionic compounds. The ion exclusion chromatography is carried out in the range of about 5.0 to about 10.0, or any pH value therebetween, for example at a pH from about 6.0 to about 10.0, a pH from about 6.5 to about 10, a pH from about 6 to about 8, or at a pH of about 5.0, 5.2, 5.5, 5.7, 6.0, 6.2, 6.5, 6.7, 7.0, 7.2, 7.5, 7.7, 8.0, 8.2, 8.5, 8.7, 9.0, 9.2, 9.5, 9.7, 10.0. To maintain the desired pH range of 5 to 10, the feed stream may be adjusted to this pH range. Those of skill in the art will be aware of chemicals suitable for adjusting the pH of the feed stream, for example but not limited to, ammonium hydroxide, sodium hydroxide, potassium hydroxide, ammonia or sulfuric acid.

The feed stream for the ion exclusion separation may arise from a variety of different streams produced during the processing of the cellulosic biomass to produce sugar. Examples of such streams are set forth in more detail below.

For example, the feed stream may be an aqueous stream obtained from the pretreated cellulosic biomass. This aqueous stream may be produced after a step of washing the pretreated biomass. Alternatively, the aqueous stream is obtained after removing solids from the pretreated biomass, for example, by centrifugation, microfiltration, plate and frame filtration, crossflow filtration, pressure filtration, vacuum filtration and the like.

For acid pretreatment, this aqueous stream may be treated with base to produce inorganic salt. Optionally, this stream may be treated with a strong acid cation exchange resin to remove metal cations from the aqueous stream prior to the treating the stream with the base.

In the case of a basic pretreatment, this aqueous stream may then be treated with one or more acid to produce inorganic salt. Alternatively, this stream may be treated with a strong acid cation exchange resin. This may involve passage of the stream through a column packed with a sulfonated polystyrene resin cross-linked with divinyl benzenes in an alkali/alkaline earth metal form. An alkali regenerant, such as sodium hydroxide, is then added to the column to produce the inorganic salt. The inorganic salt may also arise from salts that are native to the cellulosic biomass. In addition, this stream will also contain acetate or acetic acid arising from the pretreatment.

In another embodiment of the invention, the feed stream to the chromatographic separation is an aqueous stream obtained from the neutralized cellulosic biomass. In this case, the aqueous stream may be produced after a step of washing the neutralized biomass. Alternatively, this aqueous stream is obtained after removing solids from the neutralized biomass using any of the separation techniques described previously. This stream will comprise inorganic salt produced by addition of acid or base to the pretreated cellulosic biomass.

In the case of a base pretreatment, the streams obtained from the neutralized feedstock or from the pretreated feedstock will comprise a small amount of monomeric sugars, and nonionic compounds may be present. If an acid pretreatment is employed, these streams will typically comprise sugars produced as a result of the hydrolysis of hemicellulose.

In yet another embodiment of the invention, the clarified sugar stream is subjected to the chromatographic separation of the present invention. By operating at the pH range of between 5 and 10, sugars, and most other nonionic compounds present, are collected in a high-binding sugar stream, and the inorganic salt and acetate salt are collected in a separate low-binding raffinate or "salt stream". The purified sugar stream can then be fermented by microbes to produce ethanol, lactic acid, butanol or other fermentation products.

Prior to the chromatographic separation, the sugar stream may be fermented to produce a fermentation broth comprising ethanol. The fermentation broth may then be distilled to produce concentrated ethanol and still bottoms. The still bottoms stream, which comprises unfermented sugar, acetate and inorganic salts, may then be used as the feed to the chromatographic separation. Typically, the still bottoms stream is clarified prior to the chromatographic separation to remove yeast cells. This clarification step may be conducted either before or after distillation. Preferred methods for carrying out the fermentation and subsequent distillation are set forth in more detail below.

Figure 2A:
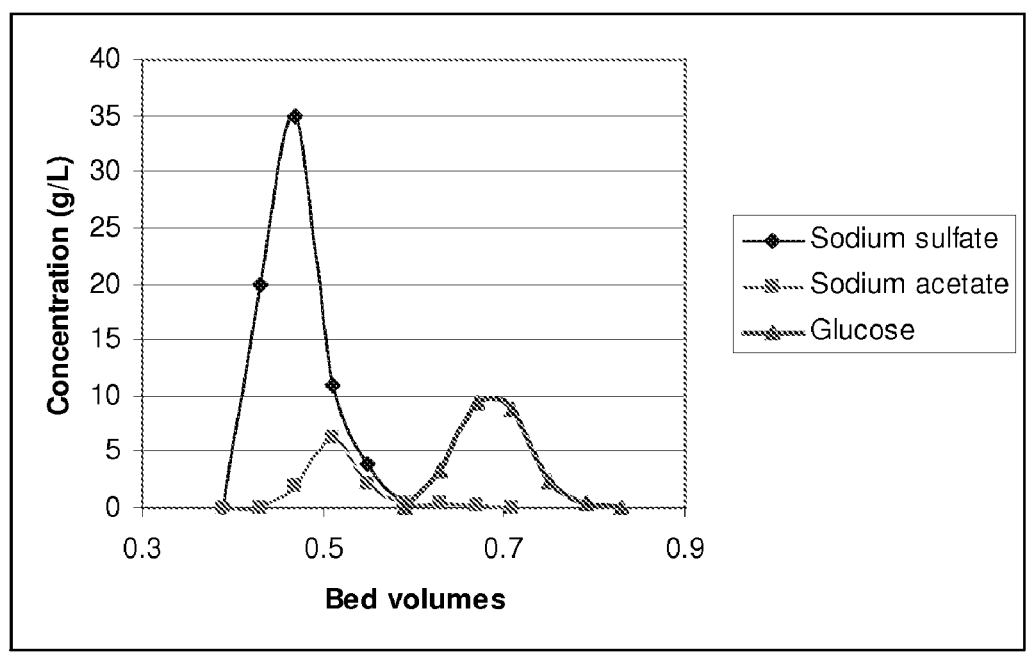
FIG. 2A shows the elution of sodium sulfate, sodium acetate, and glucose at pH 8.
Figure 2B:
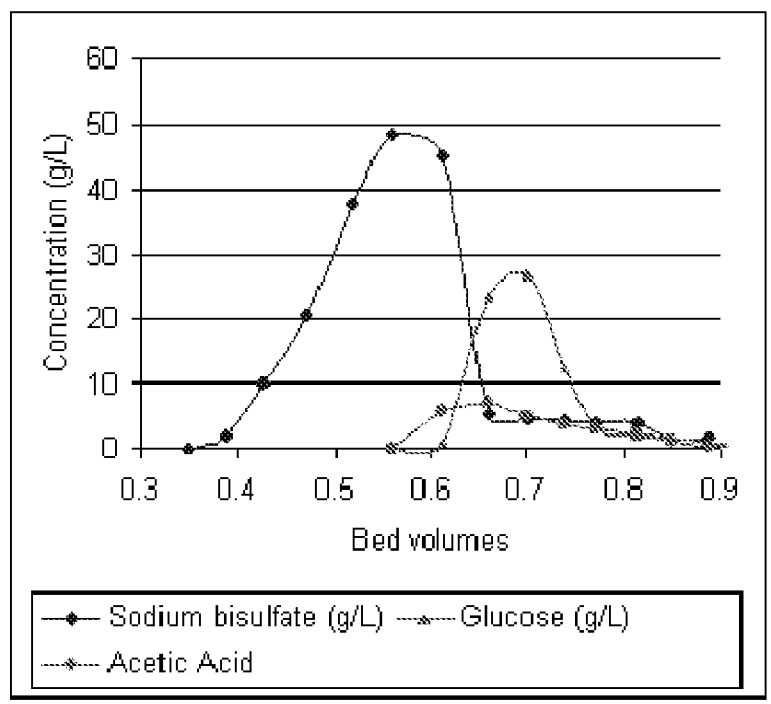
FIG. 2B shows the elution of sodium bisulfate, acetic acid, and glucose at pH 3.

The separation of sugar from sodium sulfate and sodium acetate at an alkaline pH following methods of the present invention is shown in FIG. 2A (Example 1). In addition, the separation of sugar from sodium bisulfate and acetic acid that would be present in a sugar stream arising from biomass conversion was carried out at pH 3 following the methods of Example 2. With reference to FIG. 2B, at pH 3, the separation of sugar from sodium bisulfate and acetic acid leads to undesirable separation performance under these conditions as acetic acid co-elutes with the sugar product.

The ion exclusion system of the present invention may be operated in a temperature range of about 20° C. to about 90° C., preferably at a temperature between about 45° C. to about 80° C., or any value therebetween, for example, at a temperature of about 60° C. to about 70° C., or at about 45, 47, 50, 52, 55, 57, 60, 62, 65, 67, 70, 72, 75, 77, 80° C.

The stream fed to the chromatographic separation of the present invention may contain water as a primary component. For example, the amount of water present in the crude sugar stream may be an amount in the range of about 40% to about 95% (w/w), or any amount therebetween. Preferably, the crude sugar stream may comprise from about 50% to about 85% (w/w) water, or any amount therebetween, arising from a step of concentration.

The feed stream may be concentrated using any technique known to those of skill in the art. For example, concentration may be carried out by subjecting the feed stream to membrane filtration, evaporation, or a combination thereof. Without being limiting, microfiltration (with a pore size of 0.05 to 5 microns) may be carried out to remove particles, followed by ultrafiltration (500-2000 mw cut off) to remove soluble lignin and other large molecules and reverse osmosis to increase the solids to a concentration of about 12 to about 20%, or any amount therebetween, followed by evaporation.

The feed stream should not contain any significant amount of insoluble compounds, as the insoluble compounds foul the ion exclusion chromatography system. Any suitable method for removing insoluble residue from the feed streams to produce a clarified feed stream can be employed as would be known by one of skill in the art. This includes, but is not limited to, microfiltration, plate and frame filtration, cross-flow filtration, pressure filtration, vacuum filtration, centrifugation, and the like.

It is preferred that the feed stream is characterized as having a lignosulfonate content of less than 4% of the total dry solids of the clarified sugar stream. For example, the feed stream may be characterized as having an amount of lignosulfonate from about 0 to about 4% of the total dry solids of the clarified sugar stream.

The process of ion exclusion chromatography may involve the use of one, or more than one, column filled with ion exchange resin, as is evident to one of skill in the art. For the sake of simplicity, the operation of a single column will be illustrative, but the use of more than one column is also considered to be within the scope of the present invention. The ion exchange resin is a cation exchange resin. Preferably, the resin is a strong cation exchange resin, for example, which is not to be considered limiting, with a polystyrene backbone and 4-8% divinylbenzene crosslinking. These resins have sulfonate functional groups and are available commercially in the sodium form, or, less preferably, in the hydrogen, potassium or ammonium form. The resins are preferably of diameter of from about 0.1 to about 1.0 mm. Cationic exchange resins are available from several vendors, including Dow or Mitsubishi.

The column may be prepared prior to carrying out the separation by converting it into the desired cation-exchange form. This may involve washing a volume of the clarified sugar stream through the column. The volume may be equal to from about 2 to about 5 times the volume of the resin in the column, or the washing may be carried out until the effluent pH matches the pH of the clarified sugar stream. Alternatively, the column may be prepared by washing it with a volume of solution containing cations corresponding to those that would be present in the clarified sugar stream.

Once the column is in the appropriate cation-exchange form, the feed stream is applied onto the column.

A quantity of the feed stream equal to about 0.05 to about 0.3 times the volume of the column, or any amount therebetween, is applied. However, the amount of the feed stream to be applied may differ from that just disclosed, and it may be readily determined based on experimentation to determine column capacity and separation. A desired liquid flow rate is also selected as may be readily determined by one of skill in the art, for example, but not limited to, a liquid flow rate corresponding to about 5% to about 70%, or any amount therebetween, of the column volume per hour.

As the feed stream is applied, the charged ions in the salts and other charged compounds are excluded from the resin and flow through the column. The sugar or nonionic compounds present in the feed stream are not repelled by the charged resin, and penetrate the pores of the resin. The sugar or nonionic compounds are thereby retained by the resin and elute the column more slowly than the ionic compounds.

After the desired volume of the feed stream is injected, the feed is switched to water, which may have been previously softened to decrease the concentration of multivalent cations. The ionic compounds contain inorganic salts such as the inorganic salts of the base or acid used for pH adjustment and the inorganic salts of the acid or base used in pretreatment, as well as acetic acid and other organic acids originating from the cellulosic biomass. The ionic compounds flow through the column and are collected in one or more than one stream. This one or more than one stream is designated as a "raffinate stream" or "salt stream" (or one or more than one raffinate) and contains the majority of the inorganic and acetate salts, and trace amounts of sugar or other nonionic compounds. The one or more than one raffinate stream is followed by the elution of sugars arising from the processing of the cellulosic biomass or nonionic compounds, which are collected separately from the one or more than one raffinate. The purified sugar stream contains most of the sugar and little of the salt and other ionic components.

In a preferred embodiment, the ion exclusion chromatography is carried out by a Simulated Moving Bed (SMB) device. An SMB contains ion exchange resin similar to that in an ion exclusion system described above, and performs the same type of separation of sugars and nonionic compounds in the product stream and salts and other ionic compounds in the raffinate stream. For a given feed stream, an SMB is run at the same pH and temperature as an ion exclusion system.

However, an SMB system has distinct locations for feeding of the clarified sugar stream, feeding of dilution water, and withdrawal of sugar product and of the one or more than one raffinate streams. For example, which is not to be considered limiting, four flow locations equally spaced apart may be used on one or more than one column. The order of the locations is, arbitrarily starting from the feed inlet, 1) the clarified sugar stream feed, 2) the raffinate withdrawal, 3) the dilution water feed, and 4) the product withdrawal. If a single column is used, the outlet from the top of the column may be used to feed the bottom, thus completing a circle. If more than one column is used, which is typical, the outlet of each column feeds the next column, again producing a circle of flow. The SMB is therefore much more of a fully continuous operation than a single-column ion exclusion system. Additional flow locations may be included if more than one raffinate stream is to be collected.

Another difference between an SMB and a single-column ion exclusion system is that the SMB has a recirculation flow that supplements and is co-current with all of the other flow streams. This recirculation flow is carefully chosen, along with the other flows, to provide the optimum separation between the sugar and salt streams.

Additionally, an SMB system simulates movement of the resin bed in a direction opposite to that of the liquid flow. With reference to FIG. 1, the simulated movement is carried out by periodically shifting the four flow locations by some fraction of the total bed. For example, if an SMB system is visualized as a circular system 10, for example a clock, then liquid 20 flows counterclockwise in this system. The 12 hourly positions on the clock can symbolize an SMB with 12 zones, with the feed 30 set arbitrarily at 12 O'clock. As the liquid flows around, the raffinate 40, which has a low affinity for the resin 50, is withdrawn at 9 O'clock. Dilution water 60 is added at 6 O'clock at a flow rate that is from about 1.0 to about 4.0 fold the feed application rate. In a preferred embodiment, the dilution water flow is added at from about 1.0 to about 1.5 times the feed flow rate. The bound compounds do not have a high enough affinity to remain bound at the high flow rates present after the dilution water 60 is added. These compounds are washed off the resin 50 at the product stream withdrawal 70, positioned at 3 O'clock. After the product withdrawal 70, a relatively clean stream flows back up to 12 O'clock to continue the cycle.

At a chosen interval of perhaps 10 minutes to 4 hours, preferably 15 minutes to 2 hours, the stream positions (flow locations) are shifted clockwise to simulate movement of the bed. If the positions are shifted by 1 hour in location, the feed 30 is then at 1 O'clock, product 70 at 4 O'clock, dilution water at 7 O'clock, and raffinate 40 at 10 O'clock, and this system has shifted $1/12$ in position.

The bed positions are shifted at a frequency and to a degree that are chosen to optimize the separation of interest which depends on the affinity that the sugar and salt have for the resin, the liquid flow rates, and the cost of such a switching system. A typical SMB rotates the positions by about $1/16$ to about $1/4$ of the extent of the cycle, thereby defining from about 16 to about 4 zones, respectively. The 4-to-16 zones can be carried out on a single column. In a preferred embodiment, one column is used. This simplifies the demarcation of zones and allows for a given column to be brought off line, for cleaning or maintenance without overly disturbing the operation. For example, which is not to be considered limiting, from about 4 to about 16 columns may be used. In a more preferred embodiment, about 4 to about 8 columns are used. However, the number of columns may be adjusted as required.

Improved SMB ("ISMB") systems (available for example from Eurodia Industrie S.A., Wissous, France; Applexion S.A., Epone, France; or Amalgamated Research Inc., Twin Falls, Id.) may also be used as described herein. ISMB systems include variable flow rates of feed, dilution water, product, raffinate, or a combination thereof, or sequential periods with one or more streams closed off, with or without recirculation of the liquid in the columns, or a combination of two or more of these features. The present invention can be practiced with ISMB or SMB operations.

The sugar and feed streams, the purified sugar stream obtained after ion exclusion chromatography, or both streams, may be concentrated. Any suitable method may be utilized for concentrating these streams. This includes the methods described above.

The purified sugar stream obtained following ion exclusion chromatography is readily fermented. Prior to fermentation, the product sugar stream may be adjusted to a pH from about 4 to about 6, as desired for the particular fermentation. The product sugar stream may be concentrated by evaporation, filtration, or other methods familiar to those skilled in the art, prior to fermentation.

In a preferred embodiment, the sugar in the purified sugar stream is fermented to ethanol. Fermentation may be carried out by yeast, bacteria or other microbes capable of fermenting the product stream to a desired efficiency and yield. In a preferred embodiment, the fermentation is carried out using a genetically engineered yeast, for example, but not limited to, *Saccharomyces* or *Pichia*, or bacteria, for example, but not limited to, *Zymomonas* or *E. coli* capable of fermenting the pentose sugars xylose, arabinose, or a combination thereof, in addition to the hexose sugars glucose, mannose, galactose, or a combination thererof. Alternatively, the sugar in the product sugar stream is fermented to lactic acid. Those skilled in the art are familiar with the requirements in fermentation of sugar to produce ethanol, lactic acid or other products.

The inorganic salt in the raffinate stream or salt stream may be crystallized, dried or subjected to electrodialysis or agglomeration and granulation, and used as desired, for example, as a solid fertilizer. Alternatively, the inorganic salt may be concentrated as a wet slurry and used in a liquid form, for example, as a liquid fertilizer. Processing of inorganic salt stream may be carried out as described in co-pending U.S. patent application entitled "Recovery of Inorganic Salt During Processing of Lignocellulosic Feedstock", which is incorporated herein by reference.

Ammonium, potassium, sulfate, and phosphate salts in the raffinate stream are typically of value. Other compounds present, including salts of sodium and sulfite salts, may be of less value in fertilizer. However, these salts can be converted to forms of higher value. For example, which is not to be considered limiting, sodium salts can be converted to ammonium salts or potassium salts by the use of ion exchange, which is familiar to those skilled in the art. In this example, sodium hydroxide may be used for some or all of the neutralization of sulfuric acid during the processing of a lignocellulosic feedstock, and the sodium ion exchanged with ammonium or potassium using a cation exchange resin. The resulting ammonium or potassium salt may then be of more value as a fertilizer. Additionally, sulfite salts can be converted to sulfate salts by oxidation with air or other oxidizing agent, for example, sulfurous acid or sulfur dioxide.

The present invention will be further illustrated in the following examples.

EXAMPLES

Example 1

Ion Exclusion Separation of Sodium Sulfate, Sodium Acetate, and Glucose

The effectiveness of ion exclusion at pH 8 as a process for the removal of sodium acetate and sodium sulfate salts from glucose is illustrated by this example.

A fixed bed ion exclusion column was filled with Mitsubishi Chemical resin #UBK530. Prior to filling the column, 135 ml of the resin was suspended in 1 liter of deionized water and allowed to settle. The supernatant was decanted and the procedure carried out three times, which was sufficient to remove all visible fine particles. After decanting of the third supernatant, two resin volumes of deionized water were added to the resin, and the slurry was poured onto the 127 ml column. The column contains a hot water jacket, but the jacket was not used during the resin-loading procedure. The top of the column was sealed with a rubber stopper attached to a water pump. Care was taken to ensure that the seal was airtight.

The packed column was washed with 300 ml of degassed, deionized water. This removed dissolved gases and minimized resin channeling. If the column became overloaded with air bubbles, the resin was back-washed and the column repacked.

Once the column was degassed satisfactorily, water at 70° C. was circulated through the water jacket. The column was washed with water until the temperature of the water bath reached 70° C.

At this point, the resin was prepared with the feed solution (clarified sugar stream). For this experiment, the feed solution was a synthetic sugar stream of 1% acetic acid, 10% sodium sulfate, and 2.5% glucose (w/w) dissolved in deionized water and adjusted to pH 8.0 with 10N sodium hydroxide. The resulting concentration of sodium ions was 32.4 g/L. A volume of 200 ml of feed solution was fed onto the column at a flow rate of 1 ml/min. The effluent from the column was collected and discarded. If suspended solids formed in the feed, the feed was filtered and the flow restarted.

Once the feed volume of 200 ml was achieved, the column was washed with deionized water. The conductivity of the eluent was measured and the water wash deemed complete when the eluent conductivity matched that of the water feed. At this point, any excess water present on top of the column bed was removed by using a pipette. A weight of 6.4 grams of feed was then added to the top of the bed, and the column sealed with a stopper as before. The pump was started to pump water at a rate of 1 ml/minute. The stopcock was opened at the base of the column and 4 ml fractions collected over 4 minutes. The water feed and fraction collection were continued until 30 fractions had been collected. After the collection of the $30^{th}$ fraction, the column was washed with 300 ml deionized water prior to the next run. Care was taken to avoid drying of the resin during overnight storage.

The product fractions were analyzed for sodium sulfate, sodium acetate and glucose. For the acetate determination, the samples were adjusted to pH 3-3.5 with dilute sulfuric acid prior to injection into a gas chromatograph and detection as acetic acid.

The results of the elution are shown in FIG. 2A. The sodium sulfate and sodium acetate elute with a large degree of overlap, followed by the elution of glucose. The separation was good, in that there was little glucose with the salts and little salt with the glucose.

Example 2: Comparative Example

Separation of Glucose from Acetic Acid at pH 3

This example illustrates the use of ion exclusion for the separation of sugar from acetic acid and sodium bisulfate at pH 3. The separation of acetic acid from glucose at pH 3.0 is poor as these two components co-elute (see FIG. 2B). The use of the methods as described herein, provide superior separation of acetic acid and sugar.

A fixed bed ion exclusion column was filled with Mitsubishi Chemical resin #UBK530. Prior to filling the column, 135 ml of the resin was suspended in 1 liter of deionized water and allowed to settle. The supernatant was decanted and the procedure carried out three times, which was sufficient to remove all visible fine particles. After decanting of the third supernatant, two resin volumes of deionized water were added to the resin, and the slurry was poured onto the 122-ml column. The column contains a hot water jacket, but the jacket was not used during the resin-loading procedure. The top of the column was sealed with a rubber stopper attached to a water pump. Care was taken to ensure that the seal was airtight.

The packed column was washed with 300 ml of degassed, deionized water. This removed dissolved gases and minimized resin channeling. If the column became overloaded with air bubbles, the resin was back-washed and the column repacked.

Once the column was degassed satisfactorily, water at 70° C. was circulated through the water jacket. The column was washed with water until the temperature of the water bath reached 70° C.

At this point, the resin was equilibrated with the feed solution. For this experiment, the feed solution was a synthetic sugar stream of 25 g/L acetic acid, 150 g/L sulfuric acid, and 75 g/L glucose dissolved in deionized water and adjusted to pH 3.0 with 10N sodium hydroxide. The resulting concentration of sodium bisulfate was about 190 g/L. A volume of 200 ml of feed solution was fed onto the column at a flow rate of 1.6 ml/min. The effluent from the column was collected and discarded. If suspended solids formed in the feed, the feed was filtered and the flow restarted.

Once the feed volume of 200 ml was achieved, the column was washed with deionized water. The conductivity of the eluent was measured and the water wash deemed complete when the eluent conductivity matched that of the water feed. At this point, any excess water present on top of the column bed was removed by using a pipette. A weight of 6.4 grams of feed was then added to the top of the bed, and the column sealed with a stopper as before. The pump was started to pump water at a rate of 1.6 ml/minute. The stopcock was opened at the base of the column and 4.8 ml fractions collected over 3 minutes. The water feed and fraction collection were continued until 30 fractions had been collected. After the collection of the 30$^{th}$ fraction, the column was washed with 300 ml deionized water prior to the next run. Care was taken to avoid drying of the resin during overnight storage.

The product fractions were analyzed for sodium bisulfate concentration, acetic acid, glucose, and dry weight. For the acetic acid determination, the samples were adjusted to pH 3-3.5 with dilute sulfuric acid prior to injection into a gas chromatograph.

The results of the elution are shown in the FIG. 2B. Most of the sodium bisulfate elutes before glucose is recovered. However, a portion of the sodium bisulfate co-elutes, and is present in samples comprising glucose. Furthermore, the separation of glucose and acetic acid is poor, and a significant portion of acetic acid co-elutes with glucose. This is attributed to the non-ionic nature of acetic acid at pH 3, which makes it difficult to separate from glucose at this pH. This is in contrast with Examples 1 and 3 that show a significantly improved separation of sodium sulfate and sodium acetate from glucose at an alkaline pH, for example, but not limited to, pH 8.0.

Example 3

Elution of Biomass Sugars

Figure 3:
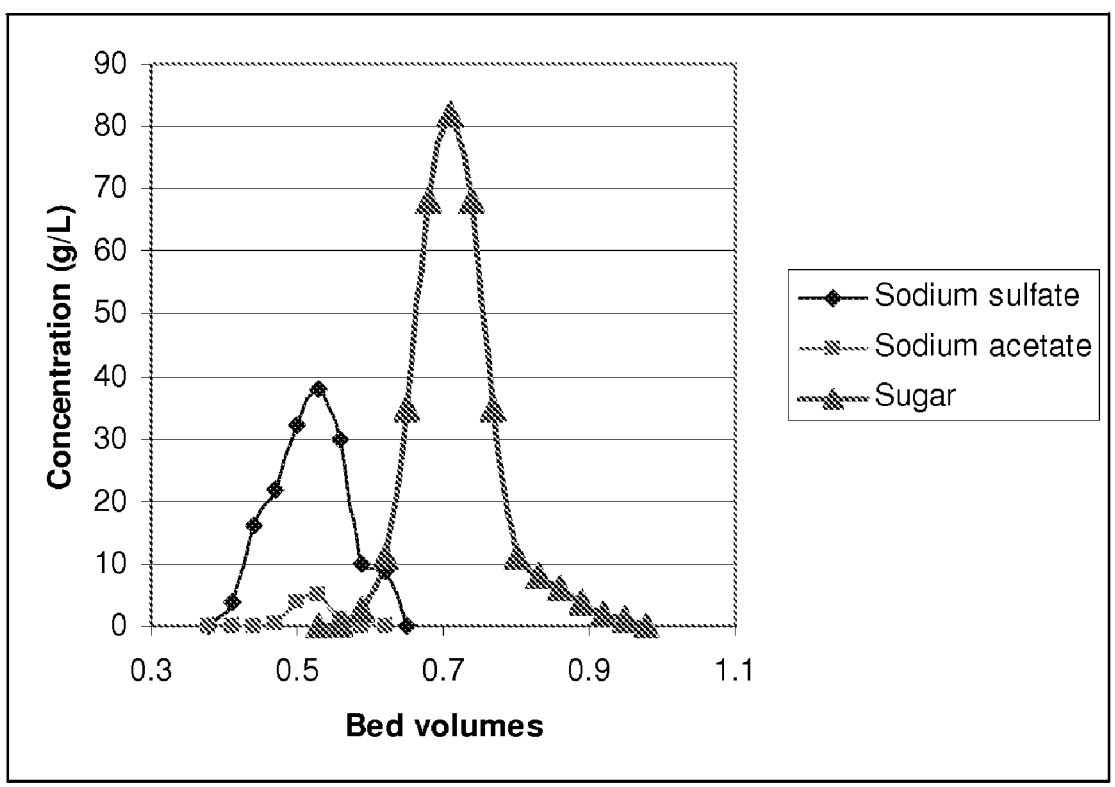
FIG. 3 shows separation of sugar (glucose, xylose and arabinose), sodium sulphate and sodium acetate in a biomass conversion clarified sugar stream using ion exclusion chromatography performed at pH 8.

A feed sample of biomass sugars was made by subjecting wheat straw to pretreatment with sulfuric acid at conditions described in U.S. Pat. No. 4,461,648. The pH of pretreatment was 1.4 and the resulting pretreated feedstock was adjusted to pH 5 with sodium hydroxide. The neutralized cellulosic biomass was subjected to enzymatic hydrolysis by cellulase enzymes made by the fungus *Trichoderma* to produce a crude sugar stream. The crude sugar stream was separated from the insoluble residue, which is primarily lignin, by using plate and frame filtration. The clarified sugar stream was evaporated to 44% total solids, with a concentration of 109 g/L sulfate salts of sodium and potassium, 300 g/L glucose, 44 g/L xylose, 5.3 g/L arabinose, 10.9 g/L sodium acetate (measured as acetic acid), and various trace metals. The clarified sugar stream was evaporated, adjusted to a pH of 8 and then fed to the column and eluted as described in Example 1. The results are shown in FIG. 3.

The ion exclusion system provides a good separation of the sugar from the sodium acetate and sodium sulfate. Almost all of the sugar is in the sugar stream, and almost all of the salt is in the salt stream. This is the case even when the sugar stream is from a biomass conversion process.

Example 4

Large Scale Purification of Sugars from Cellulose and Fermentation to Produce Ethanol A feed stream of sugars from cellulose was prepared using the procedures from Example 2 with a concentration of 145 g/L sulfate salts of sodium and potassium, 153 g/L glucose, 49 g/L xylose, 7.3 g/L arabinose, 9.1 g/L sodium acetate (measured as acetic acid), various trace metals, and a significant amount of unidentified impurities. This feed stream was divided into two parts. The first part was diluted 1:3 in water and set aside for fermentation, with a concentration of 48.4 g/L sulfate salts of sodium and potassium, 51 g/L glucose, 16 g/L xylose, 2.6 g/L arabinose, 3.1 g/L sodium acetate. The second part was subjected to large scale ion exclusion chromatography.

The chromatography was carried out on an Improved Simulated Moving Bed (ISMB) system (Eurodia Industrie S.A. of Wissous, France, available through Ameridia, Somerset, N.J.) of volume 6700 liters, packed with cation exchange resin from Mitsubishi Chemical, resin #UBK530. The ISMB system consists of 4 columns with 4 bed shifts per cycle and was operated with the feed stream maintained at pH 7.5 to 8.0. The system was maintained at 70° C. as was the sugar feed and the dilution water. The sugar stream was fed at an average rate of 4 liters per minute and dilution water was added at a ratio of 4:1 with the sugar feed. Product and raffinate streams were collected, with the product stream containing 1.6 g/L sulfate salts, 66 g/L glucose, 22 g/L xylose, 3.3 g/L arabinose, and 0.09 g/L acetate (measured as acetic acid).

Both the diluted feed stream and the product stream were pumped into fermentation vessels in liquid volumes of 100 liters and total volume 200 liters. The fermenters were inoculated with 4 g/L yeast strain 1400-LNHST obtained from Purdue University. This strain has been developed to ferment glucose and xylose to ethanol, as described in U.S. Pat. No. 5,789,210. The yield of ethanol for both treated and untreated product streams are provide in Table 1.

TABLE 1

Ethanol yields from treated and untreated sugar streams

| Sugar stream | Ethanol (g/L) after 48 hrs | Ethanol Yield (g/g initial glucose and xylose) |
|---|---|---|
| Diluted, untreated sugars | 12.2 | 0.182 |
| Ion exclusion-treated sugars | 37.9 | 0.431 |

The ion exclusion treated sugar stream was essentially completely fermented by the yeast. Without wishing to be bound by theory, the reduced yield of ethanol produced using the untreated sugar stream may be a result of inhibitors present in this feed stream. The ion exclusion treated stream resulted in a much higher yield of ethanol as shown in Table 1, possibly due to reduced amounts of inhibitors in the ion exclusion-treated stream. This is a demonstration of the detoxification of the sugar stream and the removal of acetate salts, and possibly other inhibitors, by the ion exclusion treatment.

Example 5

Separation of Salts from Xylose at pH 7

Wheat straw was leached according to the methods described in WO 02/070753 (Griffin et al.) to remove inorganic salts. A feedstock sample of biomass sugars was then produced by subjecting the leached wheat straw to pretreatment with sulfuric acid at conditions described in U.S. Pat. No. 4,461,648 (Foody). The pH of the pretreatment was 1.4 and the pH was adjusted with ammonium hydroxide to a pH value of between 4.5 and 5.0. The pretreated feedstock was subjected to enzymatic hydrolysis by cellulase enzymes made by the fungus *Trichoderma* to produce a crude sugar stream.

The resulting crude sugar stream was separated from the unhydrolyzed residue, which is primarily lignin, by using plate and frame filtration. After filtering, the clarified sugar stream was evaporated under vacuum at a temperature of between 65 to 75° C. to increase the solids content by 3-4 fold. The concentrated hydrolyzate was then filtered by plate and frame filtration. The glucose in the clarified sugar stream was fermented to ethanol with *Saccharomyces cerevisiae* yeast. While the glucose is easily fermentable, xylose sugars present in the hydrolyzate are more difficult to ferment.

After fermentation, the fermentation broth was filtered and then centrifuged to remove yeast cells. The pH was then adjusted to 7.0 with ammonium hydroxide. The fermentation broth was distilled to produce fuel grade ethanol and still bottoms, which were then evaporated to 13% total solids (w/w). The concentrated still bottoms contained 44 g/L sulfate salts of sodium, potassium and ammonium, 0.4 g/L glucose, 12.1 g/L xylose, 0.3 g/L arabinose, 9.3 g/L acetic acid, and various trace metals. The still bottoms were then adjusted to pH 7 with a small volume of 1 M NaOH and filtered. Ion exclusion chromatography of the concentrated still bottoms was performed as in Example 1, except that ammonium sulfate was passed through the column prior to addition of the sugar stream to convert the resin into the ammonium form.

The total solids content of each fraction were measured by placing 1 ml from each fraction in a pre-weighed aluminum tray and allowing them to evaporate in an oven at 100° C. for at least an hour. The trays were allowed to cool briefly before being re-weighed, and the mass difference was divided by the volume to obtain the concentration of total dissolved solids in g/L.

For xylose analysis, an aliquot of each fraction that contained dissolved solids was assayed for reducing sugars using the DNS (3,5-dinitrosalicylic acid) method described by Miller, G. L. (*Anal. Chem.*, 1959, 31:426).

Figure 4:
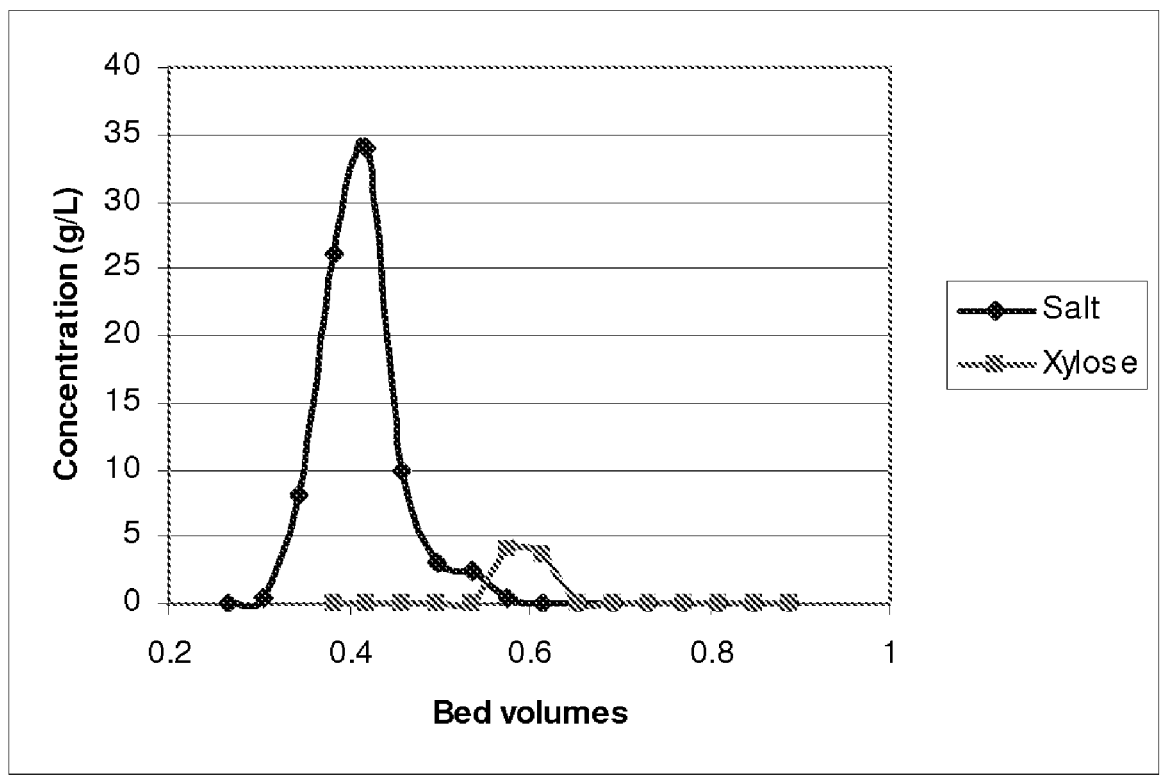
FIG. 4 shows the elution of xylose and salts in a biomass conversion process stream using ion exclusion chromatography performed at pH 7.

The results of the elution are shown in FIG. 4. Salt eluted first, followed by the elution of xylose. The separation was good in that little xylose eluted with the salts and little salt eluted with the xylose.

The purified xylose is then fermented to ethanol by a yeast strain that can convert xylose to ethanol. An example of such a strain is that described in U.S. Pat. No. 5,789,210 (Ho et al.).

Example 6

Separation of Salts from Xylose at pH 5

A feed stream of sugars from cellulosic biomass was prepared using the procedures from Example 5 except that the pH of the sugar stream was maintained at pH 5 prior to feeding it to the ion exclusion column.

Concentrations of sulfate were measured by ion exchange chromatography and concentrations of ammonium were measured by colourimetric assay. Total solids were measured as described in Example 5. The results of the elution at pH 5 are shown in FIGS. 5A, 5B and 5C.

Figure 5A:
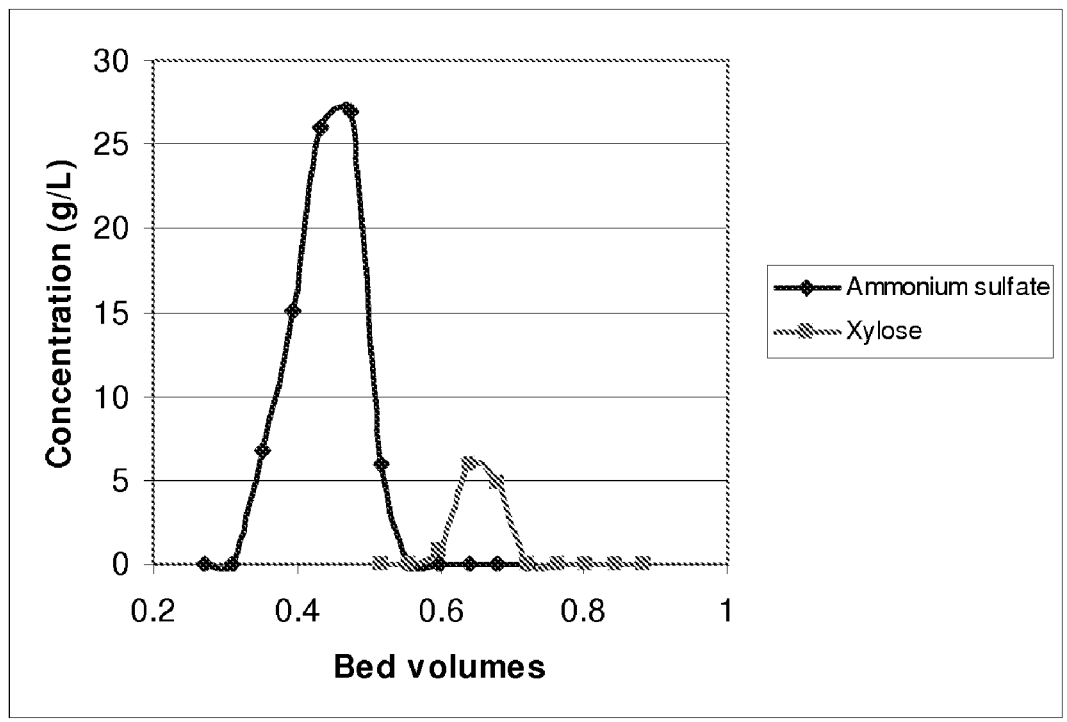
FIG. 5A shows the elution of ammonium sulfate and xylose.

As shown in FIG. 5A, the ammonium sulfate elutes first, followed by the elution of xylose. The separation was good in that there was very little bleeding of salts into the xylose peak with both the ammonium sulfate concentration and the concentration of xylose reaching close to zero between the two peaks.

Figure 5B:
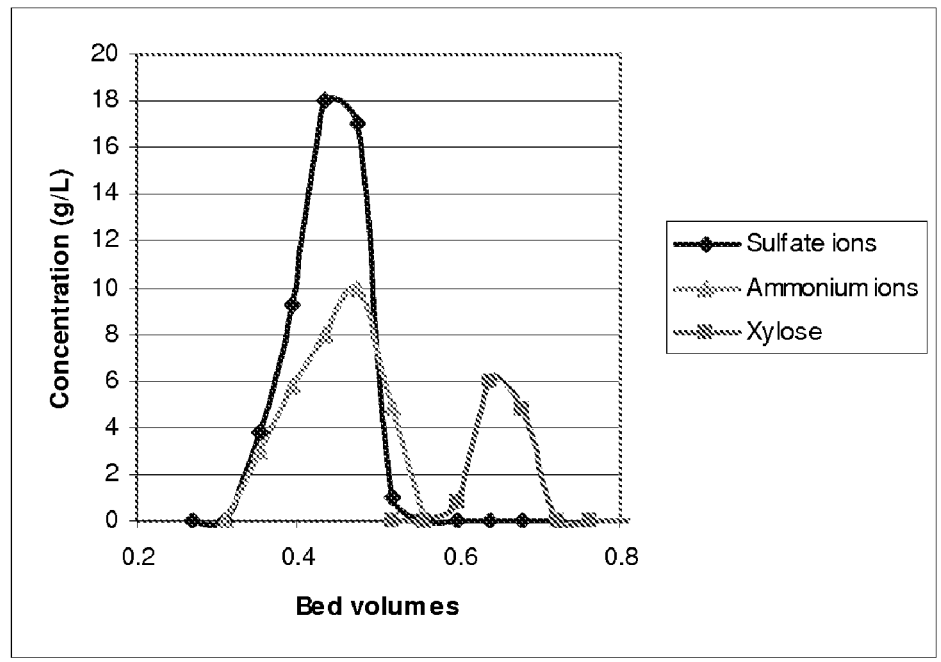
FIG. 5B shows the elution of sulfate ions, ammonium ions and xylose.

FIG. 5B shows the sulfate ion, ammonium ion and xylose content of select pulse test fractions at pH 5. The sulfate and ammonia elution peaks overlapped and were followed by an elution peak containing xylose.

Figure 5C:
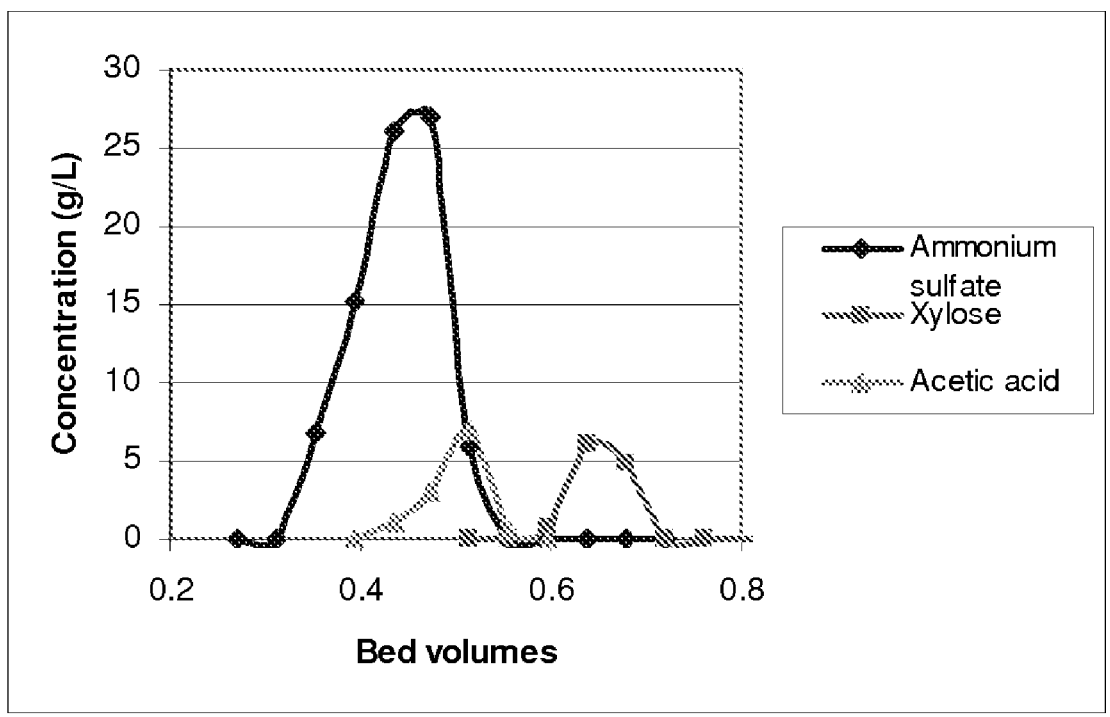
FIG. 5C shows the elution of ammonium sulfate, xylose and acetic acid.

FIG. 5C compares the elution of ammonium sulfate, xylose and acetic acid at pH 5. At this pH, "acetic acid" includes ⅓ acid and ⅔ acetate salts. As can be seen from FIG. 5C, acetic acid eluted at the end of the ammonium sulfate peak, but without bleeding into the xylose peak. The acetic acid removal from the xylose is acceptable. A larger bleeding of acetic acid into the xylose stream would be expected at a lower pH, as was observed at pH 3 in Example 2B.

Example 7

Separation of Salts from a Cellulosic Biomass Pretreated with Base

An alkaline pretreatment followed by obtaining inorganic salt and acetate salt may be carried out as follows.

Wheat straw is received in bales and chopped into pieces having a size of about 20 mesh and smaller. The chopped straw is slurried in water to reach a moisture content of about 70%. The wet straw is added to a reactor with pressurized ammonia slurry heated to 120° C. to reach a pressure of 300 psia. The mass of ammonia equals the mass of straw on a dry basis. The temperature is maintained for 20 minutes, after which the pressure is released quickly, which flashes off about 99% of the ammonia. The flash cools the reactor contents down to ambient temperature. The slurry is then adjusted to about pH 5.0 with concentrated sulfuric acid.

Upon acid addition, the soluble salt of ammonium sulfate is formed. The insoluble salt, calcium sulfate, is also formed.

The neutralized, cooled pretreated slurry is then added to a hydrolysis reactor and the reactor is mixed. The slurry will consist of 4.5% undissolved solids, and the undissolved solids will consist of 35% cellulose. Once the pretreated slurry is added to the hydrolysis reactor, cellulase and hemicellulase enzyme from *Trichoderma reesei* are added. The enzyme dosage is 35 mg protein per gram cellulose, which corresponds to a cellulase activity of 35.6 Filter Paper Units (FPU) per gram of cellulose and a xylanase activity of 275 xylanase units per gram of solids.

The hydrolysis will run for 2 days, at which point over 90% of the cellulose is converted to glucose and over 90% of the xylan is converted to xylose. The expected final glucose concentration is 6.0 to 8.0 g/L, with an average of 7.5 g/L. The hydrolysis slurry is then filtered by using a vacuum filter to separate the unhydrolyzed solid residue from the aqueous stream. The unhydrolyzed solid residue contains primarily lignin, unhydrolyzed cellulose and silica, but also the insoluble salts such as calcium sulfate. The filtrate is essentially free of insoluble particles and contains glucose, xylose, and arabinose sugar; the soluble salts ammonium sulfate, potassium sulfate, magnesium sulfate and a small amount of dissolved calcium sulfate, and acetic acid, soluble lignin, and other dissolved organics.

The process stream is evaporated to increase the solids concentration ten-fold. The expected concentrations of materials in the evaporated stream are 62 g/L glucose, 20 g/L xylose, and 2.0 g/L acetic acid. The feed stream will also contain sulfate salts of ammonium and potassium, various trace metals, and a significant amount of unidentified impurities. This feed stream will be subjected to large scale ion exclusion chromatography.

The chromatography will be carried out on an Improved Simulated Moving Bed (ISMB) system (Eurodia Industrie S.A. of Wissous, France, available through Ameridia, Somerset, N.J.) of volume 6700 liters, packed with cation exchange resin from Mitsubishi Chemical, resin #UBK530. The ISMB system will consist of 4 columns with 4 bed shifts per cycle and will be operated with the feed stream maintained at pH 7.5 to 8.0. The system will be maintained at 70° C., as will be the sugar feed and the dilution water. Product and raffinate streams will be collected, with the product stream (purified sugar stream) containing significantly reduced concentrations of sulfate salts and acetate salts (measured as acetic acid).

The product stream will be pumped into fermentation vessels in liquid volumes of 100 liters and total volume 200 liters. The fermenters will be inoculated with 4 g/L yeast strain 1400-LNHST obtained from Purdue University. This strain has been developed to ferment glucose and xylose to ethanol, as described in U.S. Pat. No. 5,789,210.

At the conclusion of the fermentation, the yeast cells are removed by centrifugation. The dilute beer is distilled to recover the ethanol from the aqueous solution, leaving still bottoms behind.

All citations are hereby incorporated by reference.

The present invention has been described with regard to one or more embodiments. However, it will be apparent to persons skilled in the art that a number of variations and modifications can be made without departing from the scope of the invention as defined in the claims.

The embodiments of the invention in which an exclusive property of privilege is claimed are defined as follows:

1. A process, comprising:
   a) pretreating the cellulosic biomass by adding a base to the cellulosic biomass to produce a pretreated cellulosic biomass comprising the acetate salt;
   b) adding an acid to the pretreated cellulosic biomass to adjust the pretreated cellulosic biomass to a pH of 4.0 to 6.0, thereby producing a neutralized cellulosic biomass;
   c) hydrolyzing the neutralized cellulosic biomass with cellulase enzymes to produce a crude sugar stream;
   d) separating insoluble residue from the crude sugar stream to produce a clarified sugar stream; and
   e) feeding an aqueous stream obtained from the pretreated cellulosic biomass, an aqueous stream obtained from the neutralized cellulosic biomass, the clarified sugar stream, or a combination thereof, to an ion exclusion chromatographic separation to produce the salt stream comprising inorganic salt and acetate salt, which ion exclusion separation is performed at a pH range between 5.0 and 10.0 using a cation exchange resin.

2. A process for obtaining ethanol or butanol by processing a cellulosic biomass, the process comprising:
   a) pretreating the cellulosic biomass by adding a base to the cellulosic biomass to produce a pretreated cellulosic biomass comprising acetate salt;
   b) adding an acid to the pretreated cellulosic biomass to adjust the pretreated cellulosic biomass to a pH of 4.0 to 6.0, thereby producing a neutralized cellulosic biomass comprising inorganic salt;
   c) hydrolyzing the neutralized cellulosic biomass with cellulase enzymes to produce a crude sugar stream;
   d) separating insoluble residue from the crude sugar stream to produce a clarified sugar stream;
   e) feeding the clarified sugar stream to an ion exclusion chromatographic separation to produce a salt stream comprising inorganic salt and acetate salt and a purified sugar stream, which ion exclusion separation is performed at a pH range between 5.0 and 10.0 using a cation exchange resin;
   f) fermenting the purified sugar stream to produce ethanol or butanol in a fermentation broth; and
   g) isolating the ethanol or butanol produced in step (f).

3. The process of claim 1 wherein, in the step of feeding (step e)), the ion exclusion chromatography is performed at a pH of between 6 and 10.

4. The process of claim 1, wherein the clarified sugar stream is fed to the ion exclusion chromatographic separation, and, wherein, said ion exclusion separation further produces a purified sugar stream.

5. The process of claim 1, wherein the aqueous stream obtained from the pretreated cellulosic biomass is produced after a step of washing the pretreated biomass, which aqueous stream is then subjected to an acid addition step.

6. The process of claim 1, wherein the aqueous stream obtained from the pretreated cellulosic biomass is produced after a step of removing insoluble solids from the pretreated biomass, which aqueous stream is then subjected to an acid addition step.

7. The process of claim 1, wherein the aqueous stream obtained from the neutralized cellulosic biomass is produced after a step of washing the neutralized biomass.

8. The process of claim 1, wherein the aqueous stream obtained from the neutralized cellulosic biomass is produced after a step of removing insoluble solids from the neutralized biomass.

9. The process of claim 1 further comprising a step of recovering the salt stream comprising inorganic salt and acetate salt.

10. The process of claim 1, wherein, during the step of feeding (step e)), the ion exclusion chromatography is carried out using a Simulated Moving Bed (SMB) system or an Improved Simulated Moving Bed (ISMB) system.

11. The process of claim 1, wherein the clarified sugar stream is characterized by having a lignosulfonate content of from about 0 to about 4% of the total solids present in the clarified sugar stream.

12. The process of claim 1, wherein the cellulosic biomass is obtained from a feedstock selected from the group consisting of an agricultural waste, corn stover, wheat straw, barley straw, canola straw, oat straw, rice straw, soybean stover, a grass, switch grass, miscanthus, cord grass, reed canary grass, a forestry residue, aspen wood or sawdust, a sugar residue, bagasse and beet pulp.

13. The process of claim 1, wherein the acid is sulfuric acid and the inorganic salt comprises a sulfate salt.

14. The process of claim 1, wherein the dosage of the cellulase enzymes is 5 to 50 IU per gram of cellulose.

15. The process of claim 1, further comprising adding at least one xylanase enzyme during said step of hydrolyzing.

16. The process of claim 1, wherein the inorganic salt is an ammonium salt.

17. The process of claim 1, wherein the cellulosic biomass is pressed or leached prior to the step of pretreating (step a)).

18. The process of claim 1, wherein the inorganic salt from the salt stream is recovered for use as a fertilizer.

19. The process of claim 1, wherein, in the step of pretreating (step a)), the base is a soluble base.

20. The process of claim 1, wherein, in the step of separating (step d)), the insoluble residue is separated from the crude sugar stream by microfiltration, plate and frame filtration, crossflow filtration, pressure filtration, vacuum filtration or centrifugation.

21. The process of claim 1, wherein insoluble residue is separated from the aqueous stream obtained from the pretreated cellulosic biomass or the aqueous stream obtained from the neutralized cellulosic biomass by microfiltration, plate and frame filtration, crossflow filtration, pressure filtration, vacuum filtration or centrifugation prior to the chromatographic separation.

22. The process of claim 1, wherein the clarified sugar stream, the aqueous stream obtained from the pretreated cellulosic biomass or the aqueous stream obtained from the neutralized cellulosic biomass is concentrated prior to or during the chromatographic separation.

23. The process of claim 3, wherein the ion exclusion chromatography is performed at a pH of between 6.5 and 10.

24. The process of claim 3, wherein the ion exclusion step is performed at a pH of between 6 and 8.

25. The process of claim 4 wherein, after the chromatographic separation, the purified sugar stream is fermented.

26. The process of claim 4, wherein the purified sugar stream is concentrated.

27. The process of claim 11, wherein the SMB system or ISMB system is operated with 4 to 16 shifts of feed and collection positions per cycle.

28. The process of claim 19, wherein the soluble base is selected from the group consisting of sodium hydroxide, potassium hydroxide, ammonia and ammonium hydroxide.

29. The process of claim 25, wherein the sugar is fermented to produce ethanol, lactic acid or butanol.

30. The process of claim 27, wherein the SMB system or ISMB system is operated with 4 to 12 shifts of feed and collection positions per cycle.

* * * * *